United States Patent [19]

Dang Vu et al.

[11] 4,268,700

[45] May 19, 1981

[54] PROCESS FOR PRODUCING GASOLINE OF HIGH OCTANE NUMBER AND PARTICULARLY LEAD FREE GASOLINE, FROM OLEFININC $C_3$-$C_4$ CUTS

[75] Inventors: Quang Dang Vu, Paris; Bernard Juguin, Rueil-Malmaison; Bernard Torck, Boulogne sur Seine; Michel Hellin, Andresy, all of France

[73] Assignee: Institut Francais du Petrole, Rueil-Malmaison, France

[21] Appl. No.: 79,728

[22] Filed: Sep. 28, 1979

[30] Foreign Application Priority Data

Sep. 28, 1978 [FR] France ................................ 78 28171

[51] Int. Cl.³ ............................. C07C 2/08; C07C 2/58
[52] U.S. Cl. ....................................... 585/302; 585/14; 585/329; 585/331; 585/332
[58] Field of Search ................. 585/14, 302, 329, 331, 585/332

[56] References Cited

U.S. PATENT DOCUMENTS 2,904,498  9/1959  Findlay .............................. 585/302

*Primary Examiner*—Curtis R. Davis
*Attorney, Agent, or Firm*—Millen & White

[57] ABSTRACT

Lead free gasoline of high octane number is obtained from $C_3$ and $C_4$ olefinic cuts as follows: propylene contained in the $C_3$ cut is oligomerized, at least 80% of the isobutene and less than 40% of the n-butenes of the $C_4$ cut are oligomerized to form an oligomerizate distilling in the gasoline range, which is separated from the unreacted $C_4$ hydrocarbons, the latter are subsequently alkylated to form a gasoline fraction which can be admixed with the oligomerizates of the $C_3$ and the $C_4$ cuts to produce the desired high octane gasoline.

13 Claims, 1 Drawing Figure

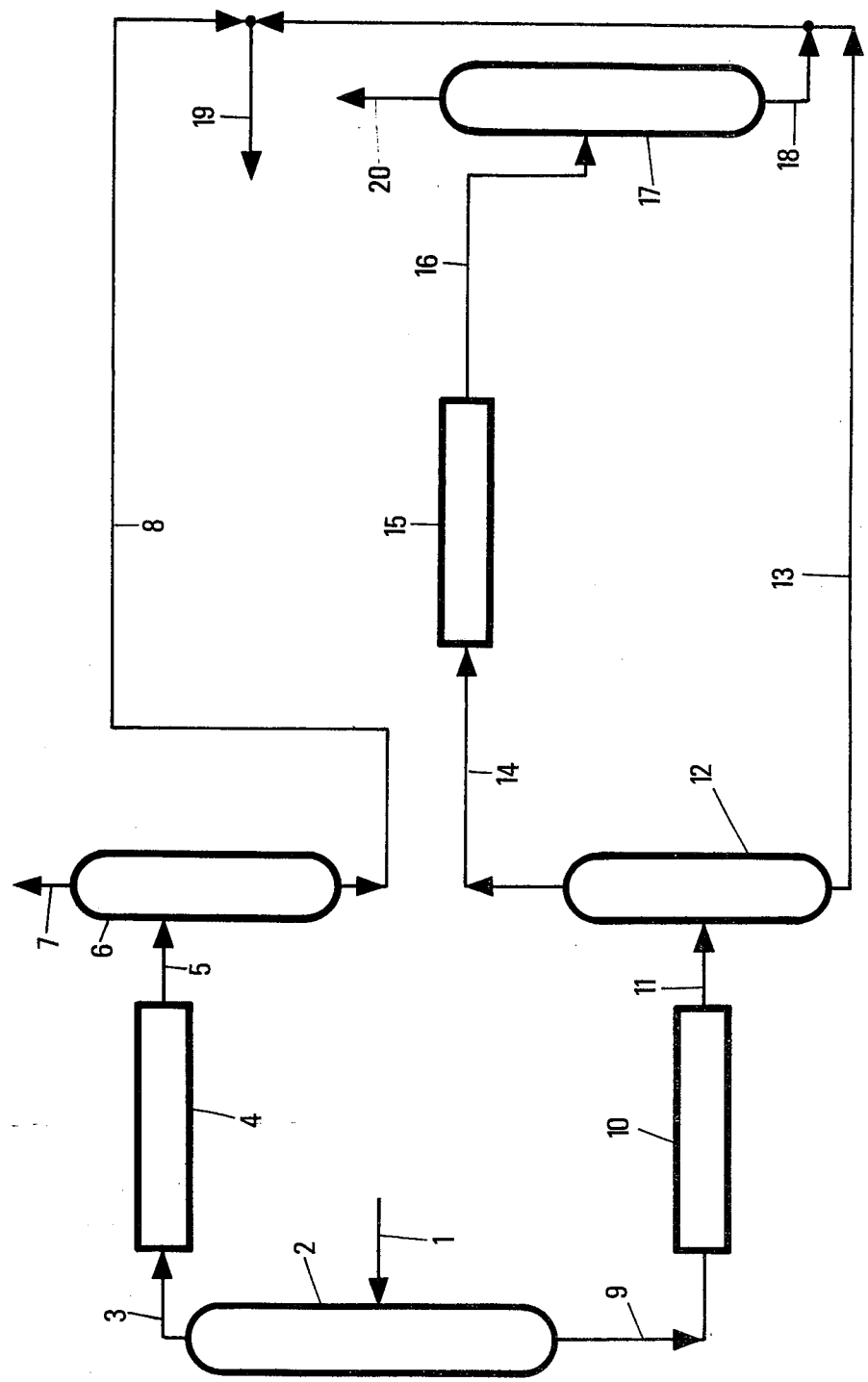

PROCESS FOR PRODUCING GASOLINE OF HIGH OCTANE NUMBER AND PARTICULARLY LEAD FREE GASOLINE, FROM OLEFININC $C_3$-$C_4$ CUTS

This invention concerns a process for producing gasoline or a gasoline component of high octane number which may be used without addition of antiknock agent such as tetraethyl lead.

THE PROBLEM

Up to now lead-free gasoline was produced in the world mainly by:
  Very severe catalytic reforming of naphtha
  Alkylation with isobutane of $C_3$-$C_4$ catalytic cracking cuts containing olefins.

Lead free gasoline, produced by high severity catalytic reforming is not ideal with respect to pollution and public health. As a matter of fact it contains benzene, whose vapor has proved very toxic.

On the contrary, alkylation yields gasoline which is satisfactory as concerns both the ecological point of view and the purely technical engine problems.

Unhappily this route is now restrained by the isobutane shortage.

More than ever it is necessary to find a process to obtain valuable products from olefinic $C_3$-$C_4$ cuts, which process is self-sufficient in isobutane and capable to yield gasoline of equivalent quality.

The reaction between isobutane and a $C_3$ or $C_4$ olefin being equimolecular the required theoretical amount of isobutane is 1.38 kg for 1 kg of propylene or 1.035 kg for 1 kg of butenes.

It has been observed that the $C_3$-$C_4$ olefinic cuts, particularly those obtained by catalytic cracking, suffer generally from the drawback of a heavy deficiency of the isobutane content which is far from being sufficient to satisfy the above stoichiometry. A typical cut has the following composition (% by weight):
  propene: 25.00
  propane: 8.35
  isobutane: 23.35
  isobutene: 10.65
  n. 1-butene: 6.65
  n. 2-butene: 18.00
  n-butane: 8.00

It is clear that the isobutane proportion is not even one third of the stoichiometrical proportion of olefins.

STATE OF THE ART

The lack of balance of $C_3$-$C_4$ cuts is well known. For example U.S. Pat. No. 3,758,628 proposes to obviate it by using simultaneously a hydrocracking unit and a catalytic cracking unit. But, as shown above, the present trend is towards a stagnation or even a reduction in the number and the capacity of existing hydrocracking units. Moreover, hydrocracking is an expensive operation which yields a number of products other than isobutane, which are not always marketable.

THE INVENTION

The present invention resolves the above problem in a new, simple and economical manner; it has for object, instead of finding an additional external source of isobutane, to modify the composition of the $C_3$-$C_4$ cut so that said composition is closer to the stoichiometrical composition in the alkylation reaction of olefins with isobutane.

It has also for object to improve the quality of the alkylate by modifying the butenes composition in such a manner that the resulting products have a higher octane number. This is achieved by alkylating $C_4$ olefins enriched with n-butenes and impoverished or made free of propylene and isobutene. As a matter of fact, the alkylates obtained by reacting isobutane with propylene or isobutene have an octane number which is not so high as those obtained by reacting isobutane with n-butenes; Research Octane Number: 92.7 when starting from isobutene, 96.8 and 96.2 respectively when starting from 1-butene and 2-butene and about 90 when starting from propylene, with sulfuric acid as catalyst.

Another object of the invention is to obtain gasoline or a gasoline component of high octane number, which can be used without lead additive.

According to the invention, the $C_3$-$C_4$ hydrocarbon charge, when not available as separate $C_3$ and $C_4$ cuts, is fractionated to a first fraction (A) of high $C_3$ hydrocarbon content, particularly of high propylene content, and a second fraction (B) of high $C_4$ hydrocarbon content, particularly of high isobutane, isobutene, 1-butene and 2-butenes content.

The first fraction (A) is selectively oligomerized essentially to $C_6$ and $C_9$ olefinic hydrocarbons, with a major portion of $C_6$ olefinic hydrocarbons, to form a first fraction (I) of gasoline of high octane number (oligomerizate I).

This is achieved by means of a specific catalyst obtained by contacting (or reacting) a transition metal compound with a hydrocarbylaluminum compound.

The second fraction (B) is subjected to oligomerization under specific conditions whereby isobutene is converted, to a larger extent than the n-butenes, in order to obtain mainly dimers and trimers but no higher oligomers. The conditions include the use of silica-alumina catalyst under moderate temperature, between 50° and 150° C.

The operation is preferably conducted with a contact time such that the conversion of the isobutene is higher than 80%, advantageously higher than 90%, the conversion of the n-butenes being however maintained below 40%, preferably below 30%. The molar ratio of isobutane to the total olefins at the outlet is preferably from 0.9 to 1.4, more preferably from 1 to 1.2.

There is thus obtained a mixture of unconverted butane and isobutane, residual n-olefins and $C_8$-$C_{12}$ oligomerizate, substantially free of isobutene. This mixture is fractionated to a top fraction including all the $C_4$ hydrocarbons and, as bottom fraction, oligomerizate II forming a second gasoline fraction as such or after hydrogenation thereof, for example, up to 75 to 80%. The $C_4$ hydrocarbons, as a result of the decrease in the olefins and particularly the isobutene content which is obtained during oligomerization by means of silica-alumina, are now in a proportion which is much closer to the stoichiometric ratio in the alkylation reaction. This composition is also more favorable for obtaining an alkylate of high octane number. It is thus convenient to feed an aliphatic alkylation unit with all these $C_4$ hydrocarbons. There is obtained an alkylate which forms the third fraction (III) of high octane gasoline.

The fractions I, II and III can then be mixed, partly or completely, in order to obtain a gasoline or a gasoline component of high octane number which can be used without lead, either as such or in admixture with, for example, a reformate or other fractions in the gasoline range.

It is possible, if so desired, to proceed to a stabilization of fractions I, II and III, either separately on each fraction or on their mixture.

DETAILED DESCRIPTION OF THE INVENTION

The hydrocarbon charge is preferably a $C_3$–$C_4$ catalytic cracking cut. It may be available as a $C_3$–$C_4$ mixture and must then be fractionated to a $C_3$ fraction and a $C_4$ fraction as abovementioned; it may also be available as separate $C_3$ and $C_4$ cuts, for example as obtained by distillation of the effluent from a catalytic cracking unit.

The catalytic cracking may be of any type, for example a fluid catalytic cracking fed with a distillate of high saturated hydrocarbon content, produced, for example, by straight run distillation of crude oils. The catalytic cracking processes are well known and a detailed description thereof is unnecessary. The catalysts are, for example, silica-alumina, a clay or a zeolite. A detailed description is given, for example, in U.S. Pat. No. 3,758,628.

The $C_3$–$C_4$ cut usually contains from 0.15 to 0.6 mole of isobutane per mole of olefins. With this condition, a typical composition by weight is as follows:
  isobutane: 15 to 30%
  propene: 15 to 35%
  isobutene: 5 to 15%
  1-butene: 3 to 10%
  2-butenes: 10 to 25%
  propane + n-butane: 8 to 30%

When the product obtained by catalytic cracking is already in the form of separate $C_3$ and $C_4$ cuts, their composition is, for example, as follows (by weight):

| $C_3$ cut : | propane | : | 15–50% |
|---|---|---|---|
| | propylene | : | 50–85% |
| $C_4$ cut : | n-butane | : | 5–20% |
| | isobutane | : | 20–50% |
| | isobutene | : | 10–25% |
| | 1-butene | : | 5–15% |
| | 2-butene | : | 10–40% |

The fractionation between $C_3$ and $C_4$ fractions is easy to achieve by distillation. It is not necessary that the $C_3$ fraction be entirely free from $C_4$ hydrocarbons nor that the $C_4$ fraction be entirely free of $C_3$ hydrocarbons.

The oligomerization of the $C_3$ hydrocarbon cut is preferably performed in the liquid phase by contacting said cut with a catalyst obtained by contacting (or reacting) a compound of a transition metal from at least one of groups IV to VIII with a hydrocarbylaluminum compound, preferably a compound of nickel with a hydrocarbylaluminum halide, for example a monohydrocarbylaluminum dihalide or a hydrocarbylaluminum sesquichloride. The reaction is conducted in most cases at a temperature from 0° to 60° C., preferably from 30° to 50° C. The nickel compound may be, for example, a carboxylate, an acetylacetonate, a phosphine complex of a nickel salt such as a chloride or an acetylacetonate. The reaction is well known and attention is called, for example, to the following patent specifications: U.S. Pat. Nos. 2,969,408 and 3,655,810, French Pat. No. 1,591,577. The state of the art is illustrated by U.S. Pat. Nos. 3,032,544; 3,390,201; 3,485,881; 3,321,546; 3,482,001 and 3,467,726.

Compounds of other metals than nickel may also be used, such as, for example, compounds of titanium (U.S. Pat. No. 3,686,350), cobalt (U.S. Pat. No. 3,686,353), chromium (U.S. Pat. Nos. 3,709,954 and 3,726,939), vanadium (U.S. Pat. No. 3,737,476), tungsten (U.S. Pat. No. 3,784,629), etc.

Preference is given to the combination of a nickel compound with a dichloroalkylaluminum, in view of its better selectivity to olefins with 6 carbon atoms.

When the oligomerization has been completed, there is obtained an oligomerizate (I) which constitutes one of the desired gasoline fractions.

Other known oligomerization techniques, for example, the treatment with a catalyst of silica-alumina, phosphoric acid, boron trifluoride, aluminum trichloride, etc. cannot be used in the present case, since the results are less satisfactory as concerns the composition of the oligomerizate which contains more of heavier oligomers having 9, 12 and 15 carbon atoms; the obtained gasoline does not comply with the conventional requirements in view of its too high end point even after admixture with the alkylate and oligomerizate II.

The oligomerization of the $C_4$ cut is achieved, under critical conditions, as above-mentioned: temperature from 50° to 150° C., preferably from 90° to 120° C. with a silica-alumina catalyst. The operating conditions are such as to provide for the oligomerization of isobutene preferably to that of the n-butenes. A partial conversion of the latter, generally in a proportion lower than 30% may be useful in some cases for further lowering the total olefin content, so that the latter is closer to the stoichiometry of the subsequent alkylation reaction.

It is important to note that this oligomerization step cannot be performed in the presence of catalysts of other types. For example of organometallic catalyst, formed by contacting a transition metal compound with a hydrocarbylaluminum compound, is not convenient due to the presence of isobutene which is converted in major part to high molecular weight polymers.

Similarly, a solid phosphoric acid catalyst is not convenient since, below about 160° C., it results in the formation of alkyl phosphates which poison the catalyst; and, above 160° C., it does not provide for a selective reaction (the conversion of the n-butenes being excessive).

It must be observed also that, even with the use of silica-alumina, an operation conducted at a temperature above 150° C. would not be sufficiently selective.

The oligomerization of the $C_4$ cut is performed, preferably, at an hourly flow rate of the hydrocarbon charge, calculated in the liquid state (VVH), of 0.2 to 10 volumes per volume of catalyst, the pressure being, for example, from 10 to 100 bars, preferably from 30 to 50 bars.

By silica-alumina catalyst, is meant a catalyst composition containing silica and alumina. It usually contains, by weight, as essential elements, from 30 to 95% of silica and from 1 to 50% of alumina, preferably 80 to 95% of silica and 5 to 20% of alumina. This catalyst may be modified by addition of other components such for example as $B_2O_3$, $TiO_2$, F, FH, $Cr_2O_3$, $ZrO_2$, $ThO_2$, MgO, Zn, Ni, Co, Pd, $Li_2O$, in a proportion up to 50% by weight of the catalyst.

A very large number of patent specifictions describe such silica-alumina catalysts and their use. Examples are U.S. Pat. Nos. 2,197,861, 2,273,038, 2,249,583 (with addition of $ZrO_2$), 2,452,190 or 2,706,211 (with Ni or Co), 2,458,818 (with MgO and $TiO_2$), 3,004,930 (with gallium halide), 3,134,824 (with $B_2O_3$, $TiO_2$, $ZrO_2$ or $ThO_2$) and 2,656,398 (with Pd).

Silica and alumina may also be in the form of an acid-treated zeolite, with or without additives, as described for example in U.S. Pat. No. 2,507,864.

The alkylation reaction is conducted under the conventional conditions for the aliphatic alkylation. There can be used catalysts known for the reaction of isobutane with butenes and preferably hydrofluoric acid with or without metal compound. Other possible catalysts are sulfuric acid, phosphoric acid or Friedel and Crafts catalysts.

When the molar ratio isobutane/$C_4$ olefins is less than 1, isobutane is preferably added to bring the ratio to at least 1.

As state of the art, there will be mentioned U.S. Pat. Nos. 2,308,560; 2,320,199; 2,429,205; 2,768,987; 2,818,458; 2,914,592; 2,920,124 and 3,855,344, among others and French Pat. No. 2,372,133 relating to hydrofluoric acid containing a metal compound.

The invention is in no way limited to particular conditions of the well known alkylation reaction. There is thus obtained an alkylate (III) constituting a third gasoline fraction of high octane number which can be admixed with the oligomerizate (I) and oligomerizate (II). Preferably at least 90% of the final gasoline distils between 40° and 220° C.

The invention is illustrated by the accompanying drawing.

A catalytic cracking effluent (line 1), or preferably a $C_3$–$C_4$ cut from said effluent, is fractionated, in a distillation unit diagrammatically shown as a column 2, into a $C_3$ and a $C_4$ fraction. The $C_3$ fraction is fed, through line 3, to the oligomerization unit 4. The effluent from said unit is supplied, through line 5, to column 6, to be fractionated. The light hydrocarbons are separated through line 7; they may be recycled to unit 4. There is recovered an oligomerization gasoline fraction through line 8. Its distillation range is between about 40° and 220° C., but it mainly contains propylene dimers. This fraction is fed to the gasoline "pool".

The $C_4$ fraction, withdrawn from line 9, is fed to the oligomerization unit 10, containing the silica-alumina catalyst. The effluent from said unit is supplied, through line 11, to the stabilization column 12. At the bottom, there is recovered the oligomerizate (II) which, if so desired, may be freed from higher oligomers which are too heavy for being kept in the gasoline. This oligomerizate is discharged through line 13. At the top there is recovered the $C_4$ cut of reduced isobutene content which is fed through line 14 to the alkylation unit 15. The alkylation effluent is fed, through line 16, to the stabilization column 17. From the top, there is withdrawn essentially n-butane and from the bottom, the desired alkylate. The latter, discharged through line 18, may join other gasoline fractions (from lines 8 and 13) to provide a gasoline usable without lead (line 19). N-butane is discharged through line 20.

EXAMPLE

The composition of the $C_3$–$C_4$ hydrocarbon charge and of the obtained fractions is given in the following Table. The operation has been conducted according to the diagram of the accompanying drawing.

The operating conditions were as follows:

First, the $C_3$ and $C_4$ hydrocarbons were separated by distillation.

The propylene oligomerization unit (4) was operated with a catalyst formed of nickel octoate and dichloroethylaluminum in an atomic ratio Al/Ni of 15:1 at a concentration of 20 parts per million of parts by weight of nickel, at a temperature of 40°–45° C., under a pressure sufficient to maintain propylene and propane in the liquid phase (about 10 bars) and with a total residence time of 3 hours. At the outlet of the reactor, the catalyst was first neutralized with anhydrous ammonia and then washed with water to remove the catalyst residues. The effluent was then fed to a stabilization column: at the top unreacted propane and propylene were recovered and at the bottom the stabilized oligomerizate.

The $C_4$ hydrocarbons were fed to the oligomerization unit 10. The operating conditions were as follows:

Catalyst: silica-alumina 90/10% by weight
Temperature: 90°–110° C.
Pressure: 40 bars
Hourly flow rate: (VVH): 2

The product obtained from said step was fractionated (column 12).

The top effluent was fed to the alkylation unit operated as follows:

Catalyst: hydrofluoric acid at a concentration of 85.9% by weight;
Temperature: 27°–38° C.;
Pressure: 14 bars;
Molar ratio isobutane/olefins of 6/1.

Counter-current reactor with recycling of unconverted isobutane.

After decantation, the organic phase was fractionated to obtain the alkylate and the isobutane to be recycled.

The alkylate was fed to a stabilization column in order to separate n-butane and traces of residual isobutane. An alkylate was recovered, which was admixed with oligomerizate (I) and stabilized and non-hydrogenated oligomerizate (II). The resultant mixture consisted of gasoline having a research octane number (RON), without lead, of 98.5. The mixture of both oligomerizates had a research octane number of 98.5 but, in admixture with the alkylate, the RON of the mixture was about 104.

The carburant mixture obtained according to the invention had a volumic mass at 20° C. of 0.707, which is typical of a light gasoline. With respect to distillation, its initial point was 40° C. and its end point lower than 200° C.

With oligomer (II) hydrogenated in a proportion of 80%, the octane number of the final mixture was substantially similar to the preceding one. As a matter of fact, in the oligomerizate mixture the research octane number (RON) of the hydrogenated oligomerizate ws lower (99 instead of 102) but, in association with oligomerizate (I), the effect of the latter substantially compensates for said reduction. Similarly, the octane number as mixture component of the combination of oligomerizate (I)+hydrogenated oligomerizate (II) was higher than that of a mixture of both oligomerizates as such.

The process of the invention may be used with $C_3$–$C_4$ olefinic cuts having another origin than catalytic cracking, for example $C_3$–$C_4$ coking cuts.

| | COMPOSITION (WEIGHT PARTS PER TIME UNIT) | | | | | | | | |
|---|---|---|---|---|---|---|---|---|---|
| | Initial charge (line 1) | $C_3$ cut (line 3) | $C_4$ cut (line 9) | Stabilized oligomerizate I (line 8) | Stabilized oligomerizate II (line 13) | Alkylation charge (line 14) | Butane cut (line 17) | Stabilized alkylate (line 18) | Final gasoline (line 19) |
| Propylene | 15.0 | 15.0 | | | | | | | |
| Propane | 5.0 | 5.0 | | | | | | | |
| Isobutane | 14.0 | | 14.0 | | | 14.0 | 0.3 | | |
| Isobutene | 6.4 | | 6.4 | | | 0.5 | | | |
| 1-Butene | 4.0 | | 4.0 | | | 2.9 | | | |
| 2-Butenes | 10.8 | | 10.8 | | | 9.7 | | | |
| n-butane | 4.8 | | 4.8 | | | 4.8 | 4.8 | | |
| Oligomerizate | | | | 14.8 | 8.1 | | | | |
| Alkylate | | | | | | | | 26.8 | |
| Total gasoline | | | | | | | | | 49.7 |

What is claimed is:

1. A process for producing high octane gasoline, comprising the steps of:
   (a) contacting an olefinic $C_3$ hydrocarbon cut comprising propylene with a catalyst, obtained by contacting at least one group IV to VIII metal compound with at least one hydrocarbylaluminum compound, in an oligomerization zone under propylene oligomerization conditions, and recovering a first oligomerizate boiling in the gasoline range;
   (b) contacting an olefinic $C_4$ hydrocarbon cut comprising isobutene, isobutane and at least one n-butene with a silica-alumina catalyst in an oligomerization zone at a temperature of from 50° to 150° C. under conditions effecting conversion of at least 80% of the isobutene and less than 40% of the n-butenes in the $C_4$ cut;
   (c) fractionating the effluent from step (b) and separately recovering a second oligomerizate boiling in the gasoline range and an unreacted $C_4$ hydrocarbon fraction comprising isobutane and at least one n-butene;
   (d) contacting the unreacted $C_4$ hydrocarbon fraction from step (c) with an alkylation catalyst in an alkylation zone under aliphatic hydrocarbon alkylation conditions, and recovering an alkylate boiling in the gasoline range; and
   (e) blending at least a portion of said alkylate with at least a portion of said first oligomerizate and at least a portion of said second oligomerizate to produce a blended high octane gasoline.

2. A process according to claim 1, wherein the $C_3$ cut used in step (a) and the $C_4$ cut used in step (b) are each produced by fractional distillation of a $C_3$–$C_4$ catalytic cracking cut.

3. A process according to claim 1, wherein the oligomerization of propylene in step (a) is conducted at a temperature of from 30° to 50° C.

4. A process according to claim 3, wherein the hydrocarbylaluminum compound is a hydrocarbylaluminum halide and the metal compound is a nickel compound.

5. A process according to claim 4, wherein the hydrocarbylaluminum halide is a dichloroalkylaluminum.

6. A process according to claim 1, wherein step (b) is effected at a temperature of from 90° to 120° C.

7. A process according to claim 1, wherein the alkylation catalyst for $C_4$ hydrocarbons in step (d) is hydrofluoric acid alone or hydrofluoric acid plus a metal compound.

8. A process according to claim 1, wherein the molar ratio isobutane/$C_4$ olefins of the unreacted $C_4$ hydrocarbon fraction from step (c) is less than 1, and isobutane is added thereto to bring the ratio to at least 1, the resultant fraction being alkylated in step (d).

9. A process according to claim 2, wherein said $C_3$–$C_4$ catalytic cracking cut has the following composition by weight:
   propylene: 15–35%
   isobutane: 15–30%
   isobutene: 5–15%
   1-butene: 3–10%
   2-butenes: 10–25%
   propane+n-butane: 8–30%.

10. A process according to claim 1, wherein the $C_3$ cut used in step (a) and the $C_4$ cut used in step (b) have respectively the following compositions, by weight:

| $C_3$ cut | | | $C_4$ cut | | |
|---|---|---|---|---|---|
| propane | : | 15–50% | n-butane | : | 5–20% |
| propylene | : | 50–85% | isobutane | : | 20–50% |
| | | | isobutene | : | 10–25% |
| | | | 1-butene | : | 5–15% |
| | | | 2-butene | : | 10–40% |

11. A process according to claim 1, wherein, in step (b), the oligomerization conditions correspond to a conversion of at least 90% of the isobutene and less than 30% of the n-butenes.

12. A process according to claim 1, wherein the molar ratio of isobutane to total olefins in the effluent from step (b) is from 0.9 to 1.4.

13. A process according to claim 1, wherein said molar ratio is from 1 to 1.2.

* * * * *

UNITED STATES PATENT AND TRADEMARK OFFICE
CERTIFICATE OF CORRECTION

PATENT NO. : 4,268,700
DATED : May 19, 1981
INVENTOR(S) : QUANG DANG VU ET AL

It is certified that error appears in the above—identified patent and that said Letters Patent is hereby corrected as shown below:

Title: reads "PROCESS FOR PRODUCING GASOLINE OF HIGH OCTANE NUMBER AND PARTICULARLY LEAD FREE GASOLINE, FROM OLEFININC $C_3$-$C_4$ CUTS"

should read -- PROCESS FOR PRODUCING GASOLINE OF HIGH OCTANE NUMBER AND PARTICULARLY LEAD FREE GASOLINE, FROM OLEFINIC $C_3$-$C_4$ CUTS -- .

Column 8, line 57: reads " 13. A process according to claim 1, wherein said "

should read -- 13. A process according to claim 12, wherein said -- .

*Signed and Sealed this*

*Twenty-eighth* Day of *July 1981*

[SEAL]

Attest:

GERALD J. MOSSINGHOFF

*Attesting Officer*     *Commissioner of Patents and Trademarks*